United States Patent [19]

Siebenthaler

[11] Plant 4,534

[45] May 13, 1980

[54] SUGAR MAPLE

[75] Inventor: John D. Siebenthaler, Dayton, Ohio

[73] Assignee: The Siebenthaler Company, Dayton, Ohio

[21] Appl. No.: 935,333

[22] Filed: Aug. 21, 1978

[51] Int. Cl.[2] ..... A01H 5/00

[52] U.S. Cl. ..... Plt./51

[58] Field of Search ..... Plt./51

*Primary Examiner*—Robert E. Bagwill

*Assistant Examiner*—James R. Feyrer

*Attorney, Agent, or Firm*—Biebel, French & Nauman

[57] ABSTRACT

A distinctive variety of sugar maple characterized by rapid growth, hardiness, uprightness, and conical shape of the tree at maturity, as well as a distinctive coloration which changes from a light green in the Autumn to a variety of mottling of gold, orange and scarlet turning to blood red.

2 Drawing Figures

1

The present invention relates to a new and distinct variety of *Acer saccharum* which is commonly called sugar maple. I discovered my new variety as a seedling mutation of unknown parentage among a group of nursery plants of the *Acer saccharum* variety which were being grown in a cultivated area of a nursery in Dayton, Ohio.

The tree is characterized by its rapid growth in early years, being more than twice in caliper, height and spread of branches when eight years old, than any other trees of the same *Acer saccharum* species around it. In addition, the opposite placement of branching forms an oval-shape as a young tree which, as the lower branches drop off as the tree matures, becomes a broad cone shaped tree at maturity. The small foliage is light green, which when cool weather comes in Autumn, turns to a distinctive variety of mottling of gold, orange and scarlet turning to blood red. A further distinctive feature is that the leaf stem or petiole is at all times a light pink in color whereas the normal leaf stem color of an *Acer saccharum* is green. I further noted that during severely cold winters where temperatures were subzero and at times below −21° F., the tree remained hardy and appeared to have suffered no damage or ill effects, no frost split or damage to terminal buds, with new growth coming up fully at the tips the following spring.

The tree of the present invention has been asexually reproduced in the above mentioned nursery, by budding.

Mature clonal trees have been observed for 15 years and have maintained their distinctive coloration. These trees, as well as younger clones, have been transplanted to determine the effect on coloration and no variation has been observed in the distinctive coloration which occurs in these clones as well.

Figure 2:
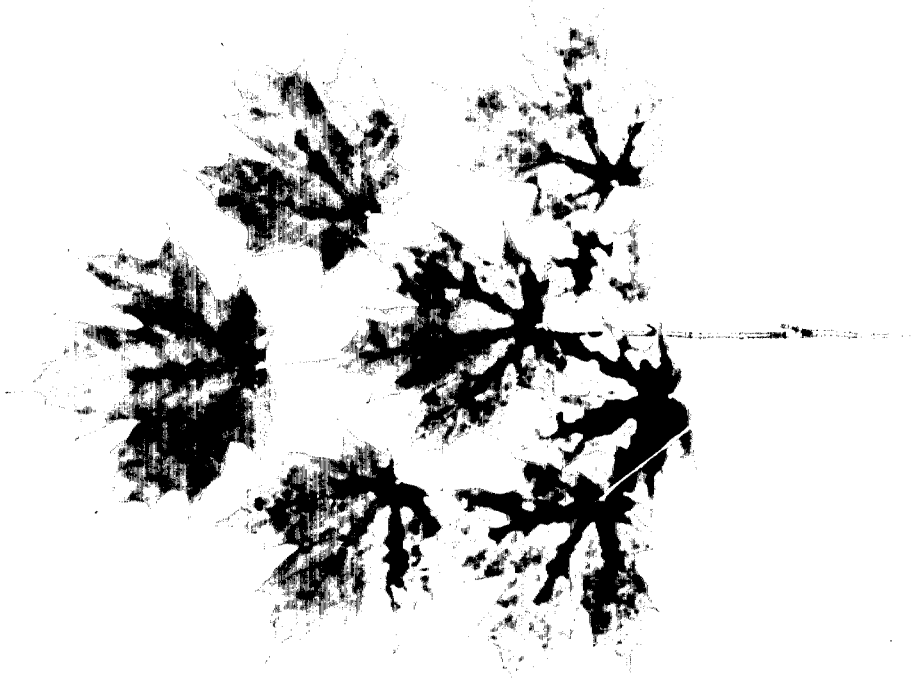
FIG. 2 is a color photograph of leaves of the tree of the present invention, taken in the fall of the year.
Figure 1:
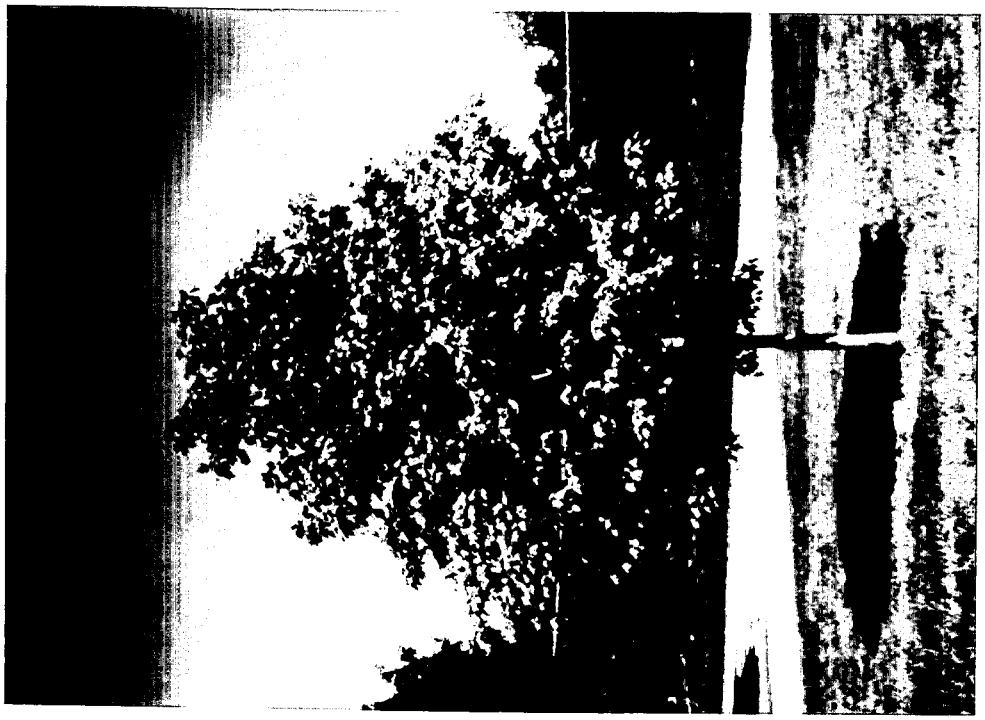
FIG. 1 is a color photograph, taken in approximately the early summer, of a young fully formed specimen of a tree of the present invention.

The following is a detailed description of my new variety of *Acer saccharum,* with color terminology in accordance with the "Royal Horticultural Society

2

Color Chart" (hereinafter R.H.S.), published by the Royal Horticultural Society of London. It is pointed out, however, that the coloration of leaves as indicated below are only approximate because the color variation is considerable as the leaves age, as indicated in that the leaves turn through a variety of mottling of colors of gold, orange and scarlet which eventually develops into the distinctive blood red color which causes a distinctive overall tree coloration easily discernable from the parent species in general. In addition, the size of leaves vary from tree to tree and in the same tree and depend to some extent on the weather during the growing season.

Parentage: A seedling mutation of unknown parentage.

Propagation: Holds distinguishing characteristics through succeeding propagation by budding.

Locality where grown and observed: Dayton, Ohio.

Tree: Upright, oval and healthy when young changing to cone-shaped with maturity.

Bark: Smoother than the species when young, but changing to the smoothness of the species when mature.

Foilage: Leaves are 3–5 lobed cordate and 3–6 inches long and 2–4 inches wide with narrow and deep sinuses; the apex and lobes are acuminate and sparingly dentate; usually glaucous and glabrous beneath.

Flowering and seeding: Same as species.

Color: As described above and more specifically, in the summer the color is Scheeles green 860/1; turning in the fall, beginning at its outer lobes and also spreading inward with markings of yellow achre 07/3 and blood red 820/2 with the latter color becoming dominant later in the season.

I claim:

1. A new and distinct variety of *Acer sacchrum* substantially as herein shown and described, characterized particularly by its rapid growth, hardiness, uprightness and conical shape of the tree at maturity and the distinctive coloration of the foliage.

* * * * *